US005691202A

United States Patent [19]

Wan et al.

[11] Patent Number: 5,691,202
[45] Date of Patent: Nov. 25, 1997

[54] SERUM-FREE MEDIUM SUPPLEMENT

[75] Inventors: Nick C. Wan, Newton; Jason C. Goodrick, Cambridge, both of Mass.

[73] Assignee: Genzyme Corporation, Framingham, Mass.

[21] Appl. No.: 591,688

[22] Filed: Apr. 26, 1996

Related U.S. Application Data

[63] Continuation of Ser. No. 410,657, Mar. 24, 1995, Pat. No. 5,512,477, which is a continuation of Ser. No. 230,933, Apr. 21, 1994, abandoned.

[51] Int. Cl.$^6$ ........................................... C12N 5/00
[52] U.S. Cl. ................. 435/391; 435/254.1; 435/257.1; 435/258.1; 435/383; 435/391; 435/404; 435/408; 435/420; 435/431
[58] Field of Search ............................ 435/391, 408, 435/404, 383, 420, 431, 254.1, 257.1, 258.1

[56] References Cited

U.S. PATENT DOCUMENTS

| | | | |
|---|---|---|---|
| 4,282,326 | 8/1981 | Moldenhauer | 435/325 |
| 5,122,469 | 6/1992 | Mather et al. | 435/325 |

FOREIGN PATENT DOCUMENTS

2251249 A  7/1992  United Kingdom.

*Primary Examiner*—Leon B. Lankford, Jr.
*Attorney, Agent, or Firm*—William G. Gosz

[57] ABSTRACT

This invention relates to a serum-free eukaryotic cell culture medium supplement. The supplement comprises carbon sources, vitamins, inorganic salts, amino acids and a protein digest.

The medium supplement of the present invention enables the maintenance of mammalian cell cultures at cell densities equal to or greater than that obtained with batch culture methods while increasing longevity and productivity.

1 Claim, 4 Drawing Sheets

SERUM-FREE MEDIUM SUPPLEMENT

This application is a continuation of U.S. Ser. No. 08/410,657 filed Mar. 24, 1995 now U.S. Pat. No. 5,512,477 which is a continuation of U.S. Ser. No. 08/230,933 filed Apr. 21, 1994, abandoned.

BACKGROUND OF THE INVENTION

Since the development of the in vitro cultivation of mammalian cells the demand for large scale production of these cells has increased due to diagnostic and therapeutic potential of many of the products they produce. These useful agents include monoclonal antibodies, human growth hormone, lymphokines, erythropoietin, blood clotting factors and tissue plasminogen activators.

For many of these cellular agents mammalian cell culture provides the only viable production source. Mammalian cells have the capability to synthesize such agents with the proper configuration, correct disulfide bonding, and arrays of sugar side chains, all of which result in the desired activity of the naturally occurring agent. Therefore, many agents derived from mammalian cells are more likely to be efficacious and are less likely to be immunogenic in target mammals if expressed by bacterial or yeast fermentation.

To improve productivity, many medium formulations for feeding of mammalian cultures have been suggested (Fike et al., *BioPharm.* Oct.: 49–54, 1993). Some suggested medium formulations using unconcentrated nutrients significantly increase the final culture volume and thus complicate the production and recovery process (Reuveny et al. *Develop. Biol. Standard* 60:185–197, 1985).

Feeding with concentrated nutrients (i.e., supplements) is the preferred in vitro cultivation strategy because the product can be recovered more economically from a smaller volume of liquid, i.e., more concentrated. Methods of supplementation involve either boosting the concentration of nutrients in a basal formulation or feeding the culture with supplements. There have been only a few reports on such feeding strategies (Jo E. C. et al., UK Patent Application #2251249A, 1992; Jo E. C. et al., Biotechnol. & Bioeng. 42:1229–1237, 1993; Luan Y. T., Biotechnol. Letters 9:691:696, 1987). However, serum has to be present in the feeding media which complicates subsequent purification procedures and increases production costs.

A need exists to develop a low-cost, serum-free supplement for use in mammalian cell cultures.

SUMMARY OF THE INVENTION

This invention relates to a serum-free eukaryotic cell culture medium supplement. The supplement comprises carbon sources, vitamins, inorganic salts, amino acids and a protein digest.

The medium supplement of the present invention enables the maintenance of mammalian cell cultures at cell densities equal to or greater than that obtained with batch culture methods while increasing longevity and productivity.

DETAILED DESCRIPTION OF THE INVENTION

Figure 1:
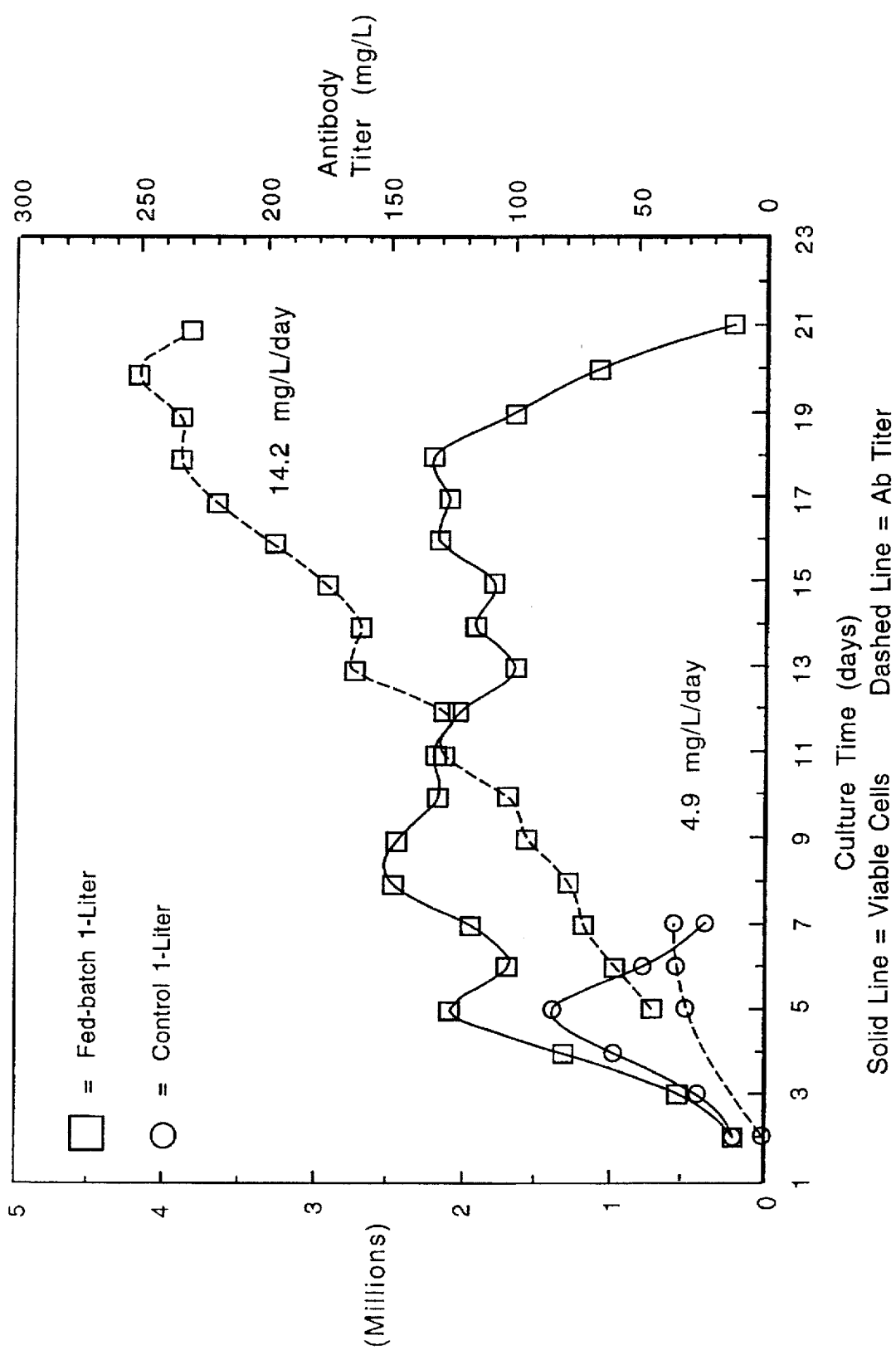
FIG. 1 shows a graph illustrating the monoclonal antibody production and cell density of one hybridoma cell line when fed with the medium supplement of the present invention versus the same culture without supplementation.
Figure 2:
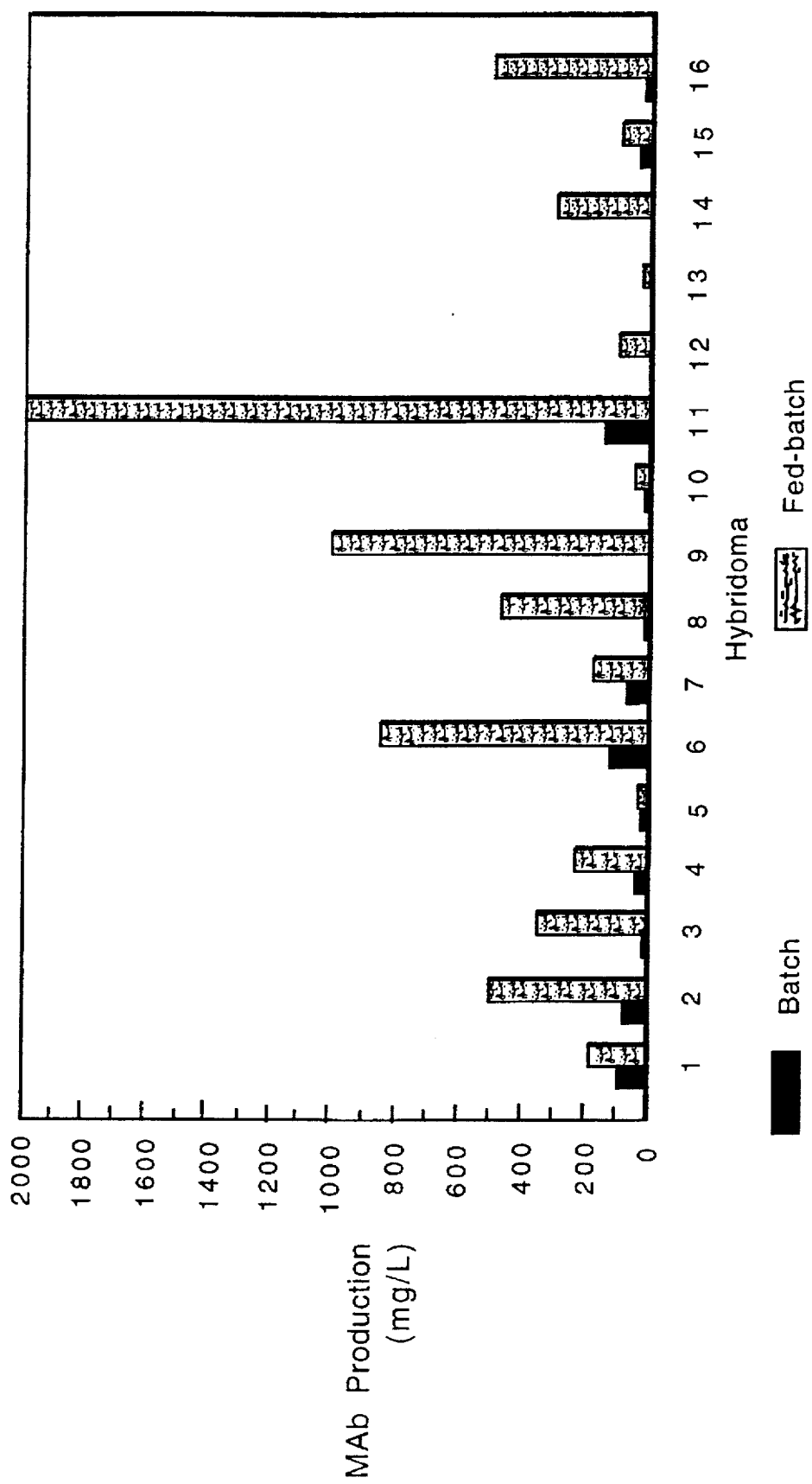
FIG. 2 shows a graph of the final monoclonal antibody production of 16 different hybridomas using fed-batch method of cell culture with the medium supplement of the present invention versus that achieved through batch culture (i.e., without supplement feeding)
Figure 3:
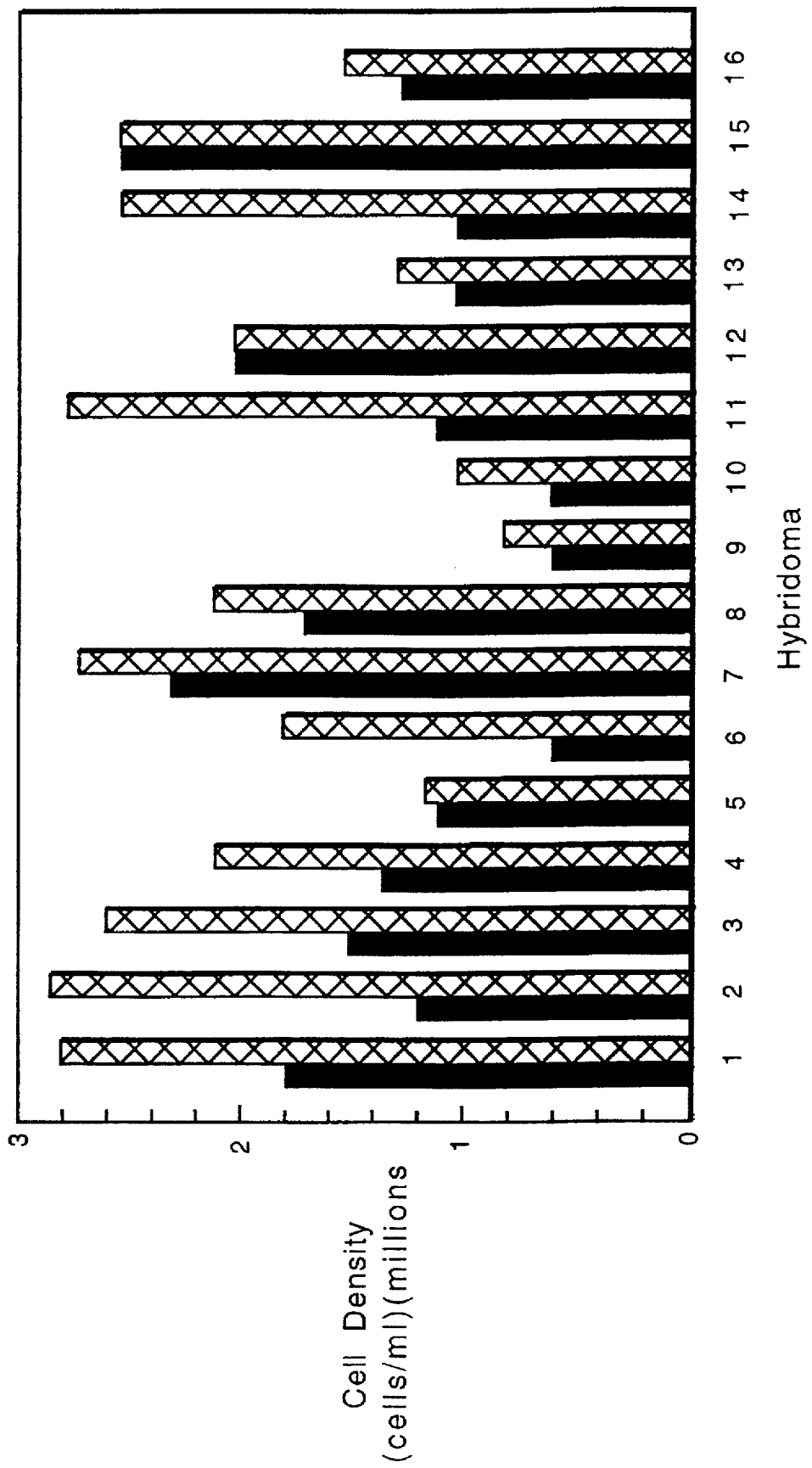
FIG. 3 shows a graph of the maximum viable cell number of the 16 hybridomas in the fed-batch mode with supplementation using the medium supplement of the present invention versus the batch method of cell culture.
Figure 4:
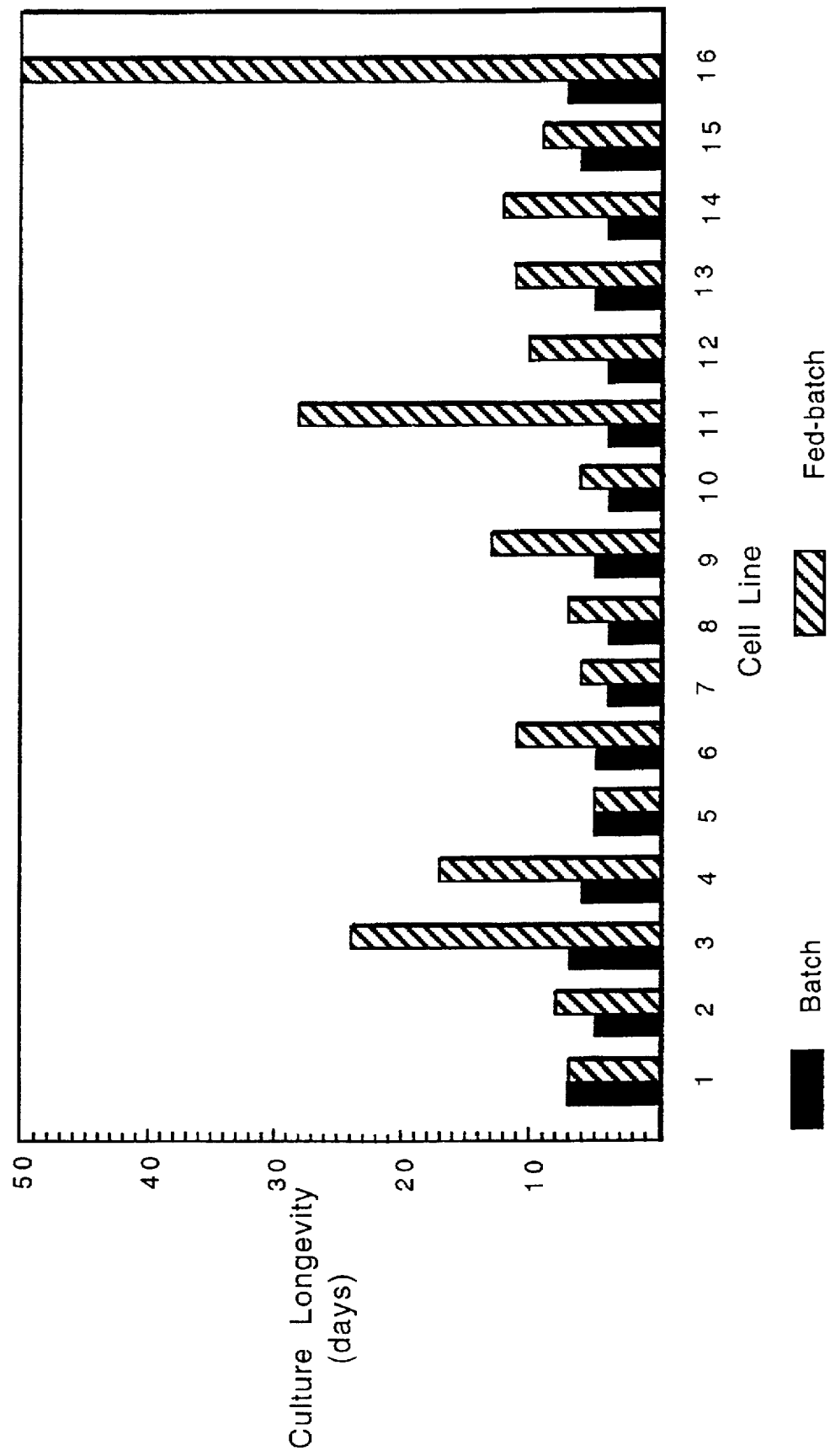
FIG. 4 shows a graph of the longevity of the 16 hybridomas in the fed-batch mode with the medium supplement of the present invention versus batch method.

This invention is based upon the discovery of a serum-free medium supplement which can be used to maintain a eukaryotic cell line in culture. The supplement comprises carbon sources, vitamins, inorganic salts, amino acids and a protein digest.

By the use of the term "supplement" what is intended is a buffered solution containing a concentrated amount of nutrients which when added to an in vitro eukaryotic cell line, maintains viability. The supplement of the present invention can be added to an in vitro eukaryotic cell culture medium without the need to remove old or spent medium.

The term "batch mode of cell culture" as used herein describes a method of culturing cells where cells are seeded into a cell culture vessel containing an initial volume of nutrient medium (such as Dulbecco's Modified Eagles Medium (DMEM) with 10% fetal bovine serum (FBS) or Protein-Free Hybridoma Medium (PFHM-II), wherein the initial volume of nutrient medium is not replenished with any medium.

The term "fed-batch mode of cell culture" as used herein describes a method of culturing cells where cells are seeded into a cell culture vessel containing an initial volume of nutrient medium and where supplements are added to the medium in a continuous or semi-continous manner.

The medium of the present invention includes a carbon source. Suitable carbon sources include L-glutamine and D-glucose. A carbon source containing L-glutamine in a concentration of about 7.3 grams per liter (g/L) and D-glucose in a concentration of 25 g/L are preferred.

The medium of the present invention, in addition, comprises vitamins. Suitable vitamins include a biotin, choline chloride, a folic acid, an inositol, a niacinamide, benzoic acid, a pantothenic acid, a pyridoxine, a riboflavin, a thiamine and B vitamin or mixture thereof. A mixture containing the vitamins listed in Table 1 below is preferred.

TABLE 1

| VITAMINS | |
| --- | --- |
| Vitamins | g/L |
| D-Biotin | 0.005 |
| Choline Chloride | 0.075 |
| Folic Acid | 0.025 |
| myo-Inositol | 0.875 |
| Niacinamide | 0.025 |
| p-Amino Benzoic Acid | 0.025 |
| D-Pantothenic Acid (hemicalcium) | 0.00625 |
| Pyridoxine HCl | 0.025 |
| Riboflavin | 0.005 |
| Thiamine HCl | 0.025 |
| Vitamin B12 | 0.000125 |

Furthermore, the medium of the present invention comprises inorganic salts. Suitable inorganic salts include potassium chloride, potassium phosphate, sodium chloride and sodium phosphate or a mixture. A mixture containing the inorganic salts listed in Table 2 below is preferred.

TABLE 2

INORGANIC SALT MIXTURE

| Inorganic Salts | g/L |
|---|---|
| Potassium Chloride | 0.05 |
| Potassium Phosphate Monobasic (anhydrous) | 0.05 |
| Sodium Chloride | 2.0 |
| Sodium Phosphate Dibasic (anhydrous) | 0.2 |

The medium of the present invention, further comprises amino acids. Suitable amino acids include alanine, arginine, asparagine, aspartic acid, cystine, glutamic acid, glycine, histidine, proline, isoleucine, lysine, methionine, serine, threonine, trytophan, tyrosine and valine or a mixture thereof. A mixture containing the amino acids listed in Table 3 below is preferred.

TABLE 3

AMINO ACID MIXTURE

| Amino Acids | g/L |
|---|---|
| L-Arginine (free base) | 2.5 |
| L-Asparagine hydrous) | 0.625 |
| L-Aspartic Acid | 0.25 |
| L-Cystine | 0.625 |
| L-Glutamic Acid | 0.25 |
| Glycine | 0.125 |
| L-Histidine (free base) | 0.1875 |
| Hydroxy-L-Proline | 0.25 |
| L-Isoleucine | 0.625 |
| L-Lysine-HCl | 0.5 |
| L-Methionine | 0.1875 |
| L-Phenylalanine | 0.1875 |
| L-Proline | 0.25 |
| L-Serine | 0.375 |
| L-Threonine | 0.25 |
| L-Trytophan | 0.0625 |
| L-Tyrosine-2Na2H$_2$O | 0.3604 |
| L-Valine | 0.25 |

In addition, the medium of the present invention comprises a protein digest. Suitable protein digests include PRIMATONE CLT™ an enzymatic digestion of meat (or meat digest), manufactured by Sheffield Products of Norwich, N.Y., casein or enzymatic hydrolysates. In a preferred embodiment the medium comprises PRIMATONE RL™ meat digest (Sheffield Products) in the amount of 25 g/L of the water component of the medium.

Exemplification

Material and Method:

Maintenance, Expansion and Feeding of Cultures

Frozen hybridoma cells (16 distinct cell lines) were thawed quickly at 37° C. and transferred into DMEM (Gibco, Grand Island N.Y.) with 10% FBS (Hyclone Laboratories Inc., Logan Utah) or PFHM-II (Gibco) and grown in t-flasks. The cells were maintained in the t-flasks at 37°±1° C. and 5–10% $CO_2$ until the cultures reached 40–70% maximum viable density.

The cells were then expanded into 1, 2, or 8-L spinner flasks with a starting viable cell density of at least 0.1–0.2 million/ml as determined by hemocytometer and trypan blue staining. The 1-L and 3-L flasks were maintained at 37±1 C. and agitated at 50–80 rpm (stir bar) with an overlay of mixed gas (5% $CO_2$, 20–40% $O_2$, balance $N_2$) at 10–20 ml/min/L. The 8–10-L flasks were agitated at 50 rpm with overhead drive and overlaid with the same gas mixture at 10–20 ml/min/L. The cultures were monitored daily as to total cell number, viable cell number, cell viability, monoclonal antibody concentration, glucose concentration, ammonia concentration, and lactate concentration.

When the viable cell density reached 50%±20% of peak density, 20 ml/L of the serum-free medium supplement, components of which are shown in Table 4 below, were added to the culture.

TABLE 4

Serum-Free Medium Supplement

| Component | g/L |
|---|---|
| L-Glutamine | 7.3 |
| D-Glucose | 25.0 |
| vitamin mixture (Table 1) | 1.0914 |
| inorganic salt mixture (Table 2) | 2.3875 |
| amino acid mixture (Table 3) | 7.8829 |
| PRIMATONE RL ™ purchased from Sheffield Products) | 25.0 |

Feeding was continued daily and D-glucose was maintained above 1 g/L (45% D-glucose solution) until the viable cell density had dropped below 0.3 million/ml. The culture was harvested, the cells removed, and the product purified from the culture with the appropriate purification procedure.

Viable Cell Count

A 0.5 to 1.0 ml sample of the culture was aseptically removed from the culture in a laminar flow hood and placed in a microfuge tube.

The cell suspension was diluted with Trypan blue/PBS (0.4%) and mix thoroughly. A cover slip was placed on a hemocytometer and a small amount of the cell mixture placed into the chambers. The chambers were allowed to be filled by capillary action. The hemocytometer was viewed under a microscope under 10×10 power and cells in all 8 of the outer boxes were counted and recorded. Both viable (clear white) and non-viable (blue) cells were counted.

viable cells #/ml =

$$\frac{\text{\# of viable cells counted}}{8 \text{ boxes}} \times \frac{1 \text{ box}}{10\text{-4ml}} \times \text{Dilution Factor}$$

$$(\%) \text{ viability} = \frac{\text{\# viable cells}}{\text{\# viable cells} + \text{\# non-viable cells}} \times 100$$

ELISA assay

Wells in polystyrene plates (cat #25801-96 high-binding flat bottom, Corning, Corning, N.Y.) were coated with 100 µl of Goat anti-mouse IgG (H+L) (Cat #115-005-003, Jackson ImmunoResearch, West Grove, Pa.), 1:200 dilution into 0.1M sodium carbonate pH 9.0, overnight at 4° C. After the overnight incubation, the liquid was removed and the plate was washed four times with phosphate buffered saline (PBS) pH 7.4 containing 0.05% Tween 20. The wells were filled with 200 µl of 2% Bovine Serum Albumin (BSA) solution in PBS to block residual binding sites. After 30 minutes incubation at room temperature (RT), the blocking reagent was removed and 100 µl of the diluted culture supernatant (PBS containing 0.05% Tween 20 and 0.5% BSA diluant) or standard antibody preparation (0 to 20 ng/ml) was added to each well. After 30 minutes incubation at RT, the plate was washed four times with the washing solution and 100 μl of peroxidase conjugated Goat anti-mouse IgG (cat #115-035-062, Jackson ImmunoResearch) diluted 1:2000 in PBS containing 0.05% Tween 20 and 0.5% BSA was added to each well. After 30 minutes incubation at RT, the plate was washed four times with the washing solution and 100 μl of OPD substrate (Cat #CIN4905/CIN4805, Medix Biotech, Inc. Foster City, Calif.) was added to each well. After 5 minutes incubation at RT, 100 μl 0.2N Sulfuric Acid was added to each well. Absorbance at 492 nm was measured in an ELISA reader and concentrations determined from the linear standard curve.

Glucose, lactate, and ammonium analysis

Glucose, lactate, and ammonium concentrations in culture samples were measured by an IBI Biolyzer (International Biotechnologies, Inc., New Haven, Conn.) following the directions provided.

Equivalents

Those skilled in the art will recognize, or be able to ascertain, using no more than routine experimentation many equivalents to the specific embodiments of the invention described herein. Such equivalents are intended to be encompassed by the following claims:

We claim:

1. A method of culturing a eukaryotic cell line, comprising adding a medium supplement comprising:

a. carbon sources consisting of about 7.3 grams/liter (g/L) of glutamine and about 25 grams/liter (g/L) of glucose;

b. vitamins consisting of about 0.005 g/L of biotin, about 0.075 g/L of choline chloride, about 0.025 g/L of folic acid, about 0.875 g/L of inositol, about 0.025 g/L of niacinamide, about 0.025 g/L of benzoic acid, about 0.00625 g/L of pantothenic acid, about 0.025 g/L of pyridoxine HCl, about 0.005 g/L of riboflavin, about 0.025 g/L of thiamine HCl, and about 0.000125 g/L of vitamin B12;

c. inorganic salts consisting of about 0.05 g/L of potassium chloride, about 0.05 g/L of potassium phosphate, about 2.0 g/L of sodium chloride, and about 0.2875 g/L of sodium phosphate;

d. amino acids consisting of about 2.5 g/L of arginine, about 0.625 g/L of asparagine, about 0.25 g/L of aspartic acid, cystine, about 0.25 g/L of glutamic acid, about 0.125 g/L of glycine, about 0.1875 g/L of histidine, about 0.25 g/L of proline, about 0.625 g/L of isoluecine, about 0.5 g/L of lysine, about 0.1875 g/L of methionine, about 0.1875 g/L of phenylalanine, about 0.375 g/L of serine, about 0.25 g/L of threonine, about 0.0625 g/L of trytophan, about 0.3604 g/L of tyrosine and about 0.25 g/L of valine; and e. 25 g/L of a meat digest, wherein the supplement maintains eukaryotic cell viability when added to the culture medium.

* * * * *